(12) United States Patent
Passilly et al.

(10) Patent No.: US 8,181,506 B2
(45) Date of Patent: May 22, 2012

(54) TIP INDENTING APPARATUS FOR TESTING A BLOCK OF MATERIAL

(75) Inventors: Bruno Passilly, Le Plessis Robinson (FR); Michel Bejet, Les Ulis (FR)

(73) Assignee: Onera (Office National d'Etudes et de Recherches Aerospatiales), Chatillon (FR)

( * ) Notice: Subject to any disclaimer, the term of this patent is extended or adjusted under 35 U.S.C. 154(b) by 418 days.

(21) Appl. No.: 12/447,412

(22) PCT Filed: Oct. 25, 2007

(86) PCT No.: PCT/FR2007/052227
§ 371 (c)(1),
(2), (4) Date: Jul. 14, 2009

(87) PCT Pub. No.: WO2008/050057
PCT Pub. Date: May 2, 2008

(65) Prior Publication Data
US 2010/0212411 A1    Aug. 26, 2010

(30) Foreign Application Priority Data

Oct. 25, 2006   (FR) ...................................... 06 09380

(51) Int. Cl.
*G01N 3/48* (2006.01)
(52) U.S. Cl. .......................................................... 73/81
(58) Field of Classification Search .................... 374/46
See application file for complete search history.

(56) References Cited

U.S. PATENT DOCUMENTS

| | | | |
|---|---|---|---|
| 2,375,033 A | 5/1945 | Parke et al. | 374/46 |
| 3,191,424 A | 6/1965 | Sakae | 374/46 |
| 5,133,210 A * | 7/1992 | Lesko et al. | 73/81 |

FOREIGN PATENT DOCUMENTS

WO    WO-91/12513    8/1991

OTHER PUBLICATIONS

International Search Report from counterpart application No. PCT/FR2007/052227; Report dated May 27, 2008.
French Preliminary Search Report from priority application FR 06 09380; Report dated Jun. 4, 2007.

* cited by examiner

*Primary Examiner* — Hezron E Williams
*Assistant Examiner* — Tamiko Bellamy
(74) *Attorney, Agent, or Firm* — Miller, Matthias & Hull LLP

(57) ABSTRACT

The invention relates to a tip indenting apparatus for testing a block of material, characterized in that it comprises: a holder for the tip and a holder for a block of a material to be punched or scratched, said tip holder and said block holder each comprising a solid body made of heat conducting material; securing means for removably securing the tip or the block in thermal-conducting contact to said solid body; an annular sheath having a shape corresponding to that of said solid body and in which said solid body is provided; heating means comprising at least one electric heater; and means for assembling the solid body and the heating means; wherein, during a test, the tip can be heated at a predetermined temperature, in particular a temperature essentially equal to that of the block of material to be tested.

29 Claims, 2 Drawing Sheets

TIP INDENTING APPARATUS FOR TESTING A BLOCK OF MATERIAL

CROSS-REFERENCE TO RELATED APPLICATIONS

This application is a U.S. national stage filing of International Patent Application No. PCT/FR2007/052227 filed on Oct. 23, 2007, which claims priority under the Paris Convention to French Patent Application No. 06 09380, filed on Oct. 25, 2006.

FIELD OF THE DISCLOSURE

The present invention relates to an indenting apparatus with a tip suitable for testing a block of material.

BACKGROUND OF THE DISCLOSURE

The field of application of the invention is more particularly an indenting apparatus suitable for punching or scratching a material with a given force of pressure or of impact with the aid of a tip, for example of the Vickers, Berkovitch, Knoop or spherical type, and, subsequently, suitable for measuring the dimensions and the volume of the trace left on the material to be tested as a result of the force of pressure or of impact that this material has sustained. It is therefore possible to determine the mechanical properties of the material, such as its hardness, its modulus of elasticity, from the shape and the depth of the imprint left in the material and from the curve (force exerted, depth) obtained during the test.

The materials to be tested and the tip are elements having dimensions that can be relatively small. It is therefore necessary to provide holder devices adapted to such dimensions.

Tip indenting items of apparatus suitable for testing a block of material are known in the prior art (U.S. Pat. Nos. 3,191,424, 3,221,535, 6,361,641).

However, these items of apparatus are not adapted for an indentation at very high temperature with very low forces of impact, in order to determine the behavior of materials at very high temperature. Very high temperature is understood to be temperatures higher than 700° C. and capable of reaching 1200° C.

Currently there are no items of indenting apparatus making it possible to determine the behavior of a material, notably at very high temperature, that has to sustain a shock or an impact.

SUMMARY OF THE DISCLOSURE

For this reason, the present invention relates to an indenting apparatus with a tip suitable for testing a block of material, characterized in that it comprises a holder for the tip arranged in the form of a holding and heating device, notably at very high temperature, and a holder for a block of a material to be punched or scratched arranged in the form of a holding and heating device, notably at very high temperature, said holder for the tip and said holder for a block each comprising a solid body made of heat-conducting material, having a peripheral side wall and a transverse face; securing means provided on said transverse face in order to secure in a removable manner either the tip, or the block of material to be punched or scratched, in heat-conducting contact with said solid body; an annular sheath of a shape to match the solid body in which said solid body is housed; heating means of annular structure suitable for tightly surrounding the side wall of the annular sheath and being in heat-conducting contact with the latter, said heating means comprising at least one electric heating member, and means for assembling the solid body and the heating means, whereby the tip may, during the test, be brought to a determined temperature, notably to a temperature substantially equal to that of the block of material to be tested.

Specifically, in order to determine the mechanical properties of a material, an indenting apparatus with a tip is routinely used. Up to now, if the user desired to know the behavior of a material at a certain temperature, but without reaching very high temperatures, the user heated only the material to be tested. For low forces of impact, and for very high temperatures, the heat transfer between the unheated tip and the heated material to be tested is likely to influence the real temperature of the material at the moment of contact of the tip with the material, a portion of the heat of the material to be tested being capable of being transferred to the tip thereby reducing the real temperature of the material to be tested. So currently it is not possible to determine the given mechanical behavior of a material at a high temperature with the aid of a tip test. Therefore, if the user desires more precisely to obtain the mechanical properties of the material at a given temperature and in order to prevent heat transfers, between the tip and the material to be tested, that are likely to influence the temperature of the material to be tested, the user makes provision to heat both the tip and the block of material to be tested, each with the aid of a holding and heating device. Currently, independent devices for holding and heating to high temperature a tip and a block of material to be tested are not known.

In order to allow the tip or the block of material to be heated in a substantially even manner and therefore to obtain a heated object having the same temperature at any given point, the heating means comprise a tubular sleeve made of heat-conducting material surrounding the annular sheath and in heat-conducting contact with the peripheral side wall of the latter, the electric heating member being wound round the tubular sleeve. However, for the object to be at one and the same temperature at any given point by thermal conduction of the heat between the tubular sleeve, the annular sheath and the object, the heating means must first be switched on before applying any force of pressure to the object, or vice versa. This gives a state of balance between these various elements and the tip or the block of material has, after a certain period of time, a substantially uniform and homogeneous temperature.

In order to allow a heat-conducting contact that can be easily adapted to any possible shape of the annular sheath, the electric heating member is a metal wire, notably a platinum wire.

For the tubular sleeve to be heated in a uniform manner over its whole height, the metal wire is helically wound around the outer wall of the tubular sleeve.

In order to achieve a heat-conducting contact as tight as possible between the tubular sleeve and the electric heating member, at least one groove is hollowed out in the outer wall of the tubular sleeve around the latter, the heating member being housed in this groove.

Advantageously, the assembly means comprise a cylinder tightly surrounding the heating means and removable means for retaining this cylinder.

In order to allow the replacement in a minimum amount of time of the electric heating member or of the tubular sleeve, the removable retaining means comprise at least one clamping rod engaged in at least one passageway passing, notably diametrically, through the solid body, the annular sheath, the heating means and the cylinder.

In order to prevent any displacement of the tip at the time of impact of the tip on the material to be tested, which would generate a margin of error with respect to the force of impact actually provided to the block of material to be tested, the means for securing the tip comprise: a recess made in the transverse face of the solid body; a core with an outer shape that matches that of the recess, the core comprising a through-passageway with a shape to match that of the tip so that the latter is received in an adjusted manner in this passageway with its pointed end protruding outside the transverse face of the solid body and its base forced into heat-conducting contact against the bottom of the recess; means for immobilizing the tip in the passageway, and means for immobilizing the core in the recess.

In order to facilitate and reinforce the effect of immobilizing the tip in the core, the bottom of the recess comprises a protruding integral axial finger with a diameter at most equal to that of the passageway, and the base of the tip is forced into heat-conducting contact against the transverse face of the finger. Therefore, a force of pressure is exerted against the bottom of the tip which tends to press the tip into the passageway and make the tip protrude from the passageway. The protruding position of the tip out of the passageway is then reinforced.

In order to allow the core to be rapidly attached to the solid body and in order to make it easier to replace one tip with another, the recess is tapped and the core is threaded and screwed into the recess.

In order to reinforce the securing and immovability of the tip in the passageway of the core, the means for immobilizing the tip in the passageway comprise a powdery material of small particle size placed in the passageway between the tip and the core.

In order to allow an irremovable connection between the block of material to be tested and the solid body when the material to be tested sustains an impact or a force of pressure, the means for securing the block of material to be punched comprise two inverted-L sections placed face to face in protrusion on the transverse face of the solid body, under which the block of material is inserted.

Advantageously, the tip is either a Vickers tip, or a Berkovitch tip, or a Knoop tip, or a spherical tip.

In order to measure the forces exerted by the tip on the material to be tested, the holder for the block of material to be scratched or punched rests on a force sensor.

According to an advantageous embodiment, the holder for the block of material to be scratched or punched rests on the force sensor via connecting means in the form of a tubular element, preferably made of zircon.

Advantageously, the deformation of the force sensor is measured continuously by a capacitive displacement sensor.

Advantageously, the force sensor rests on a cooled part.

Preferably, the tubular element passes through a cooled part.

According to a particular embodiment, the force sensor consists of a gage bridge device.

Advantageously, the indenting apparatus comprises means for viewing the holder of the block of material to be scratched or punched, notably capable of monitoring the expansion of said holder of the block of material when it is being heated.

In order to reinforce the immobilization of the block of material to be tested, the holder of the block of material to be scratched comprises screwing means passing axially through the solid body and capable of applying a pressing force on the block against the securing means.

Advantageously, the holder of the tip can be moved vertically with the aid of displacement means.

Advantageously, the holder of the block of material to be tested can be moved horizontally with the aid of displacement means.

According to an advantageous embodiment, the vertical displacement means of the holder of the tip comprise a motorized translation table and a piezoelectric translator.

Advantageously, the piezoelectric translator is linked to a displacement sensor, advantageously a capacitive displacement sensor.

The present invention also relates to a method of measuring the force exerted by a tip on a block of material to be tested with the aid of an indenting apparatus according to one of the preceding claims, characterized in that it comprises a step of measuring the displacement of the tip in the block of material and, at the same time, a step of measuring the force exerted by the tip on the block, the displacement measurement being determined by subtracting the value measured by a first displacement sensor included in the means for displacing the holder of the tip from the value measured by a second displacement sensor measuring the deformation of the force sensor supporting the holder of the block of material to be tested.

Advantageously, a force feedback loop is formed so long as the value calculated during the measurement step does not reach a fixed setpoint value.

Advantageously, the method according to the invention also comprises a step of displacing a piezoelectric translator included in the means for displacing the holder of the tip so long as the value calculated during the measurement step has not reached the fixed setpoint value.

Advantageously, the value of the displacement of the piezoelectric translator corresponds to a percentage of the difference between the fixed setpoint value and the value determined during the measurement step.

BRIEF DESCRIPTION OF THE DRAWINGS

The present invention will now be described with the aid of examples that are only illustrative and in no way limiting and based on the following illustrations, in which.

DETAILED DESCRIPTION OF THE DISCLOSURE

Figure 2:
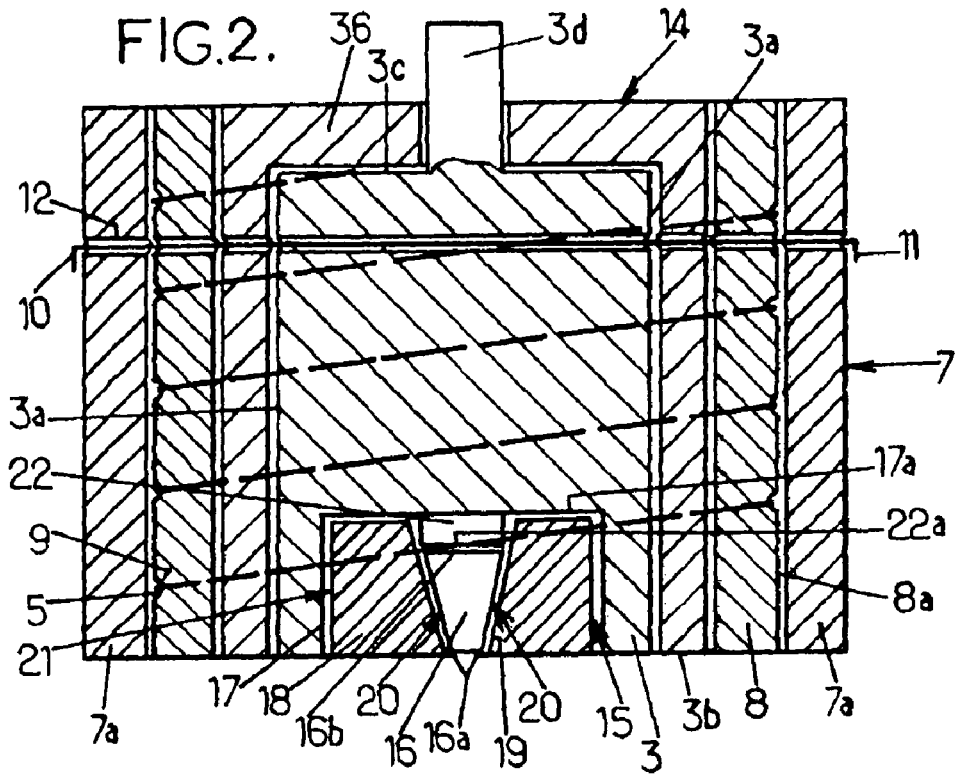
FIG. 2 is a schematic view in section of a device for holding and heating a tip of an indenting apparatus according to the invention.
Figure 1:
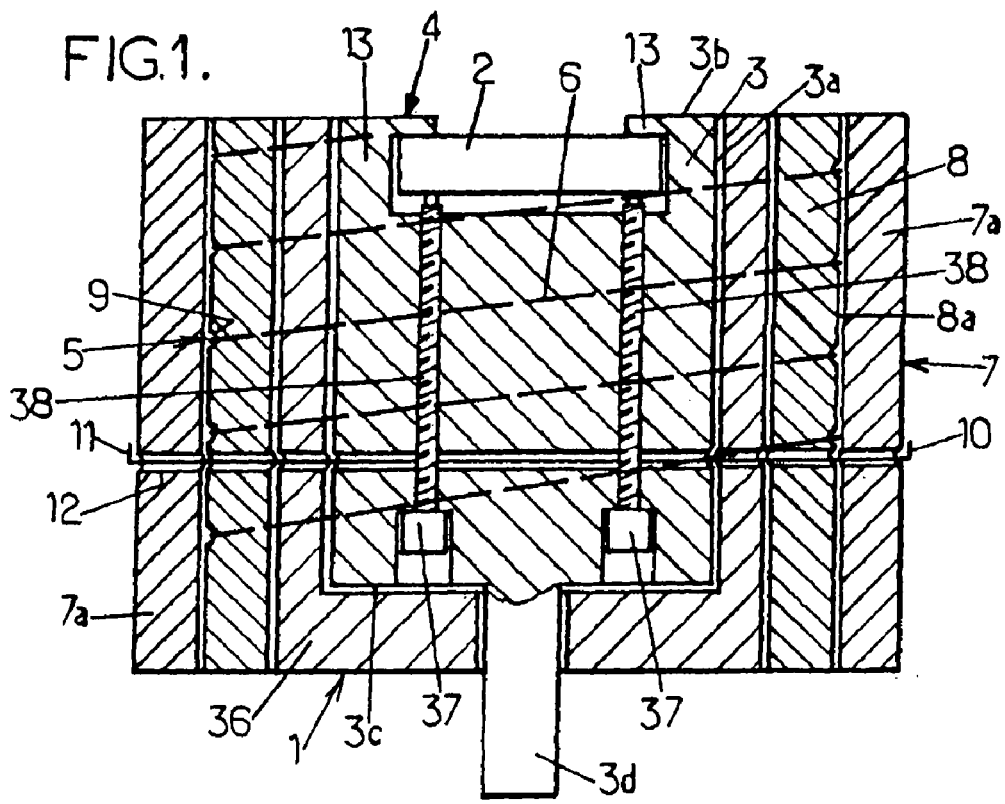
FIG. 1 is a schematic view in section of a device for holding and heating a block of material to be tested for an indenting apparatus according to the invention.

FIGS. 1 and 2 represent respectively a schematic view in section of a device for holding and heating a block 2 of material to be tested and of a tip 16 of an indenting apparatus 23 according to the invention.

More precisely, FIG. 1 illustrates, in a schematic view in section of a device 1 for holding and heating a block 2 of material to be tested, the device 1 belonging to an indenting apparatus 23 according to the invention comprising a solid body 3, advantageously made of a heat-conducting material, having a peripheral side wall 3a and a transverse face 3b. "Solid body" is understood to be any body that may fulfill the function of an anvil, that is to say any body that is able to withstand an impact or shock without deforming and serving as a means for holding an object directly sustaining a shock or impact or having to apply a shock or an impact to another object. The solid body 3 takes the general form of a cylinder and is advantageously made of a metal.

Securing means 4 are provided on the transverse face 3b of the solid body 3 in order to removably secure the object 2 in heat-conducting contact with the solid body 3.

The device 1 for holding the block 2 of material to be tested also comprises an annular sheath 36, of a shape to match the solid body 3, in which the solid body 3 is housed.

Heating means having an annular structure are provided so as to tightly surround the peripheral side wall of the annular sheath 36 while being in heat-conducting contact with the latter. The heating means 5 comprise at least one electric heating member 6.

Assembly means 7 are also provided so as to secure and keep in heat-conducting contact the solid body 3 and the annular sheath 36 with the heating means 5.

The heating means 5 comprise a tubular sleeve 8, advantageously made of a heat-conducting material, such as alumina, surrounding the annular sheath 36 and in heat-conducting contact with the peripheral side wall of the annular sheath 36.

In order to allow a homogeneous heating over the whole annular sheath 36 and the solid body 3, the electric heating member 6 is wound round the tubular sleeve 8, and more precisely it is helically wound around the outer wall 8a of the tubular sleeve 8.

In order to allow the heat-conducting contact between the heating member 6 and the tubular sleeve 8, at least one groove 9 is hollowed out in the outer wall 8a of the sleeve 8 around the latter and the heating member 6 is housed in this groove 9.

Preferably, the electric heating member 6 is a metal wire, notably a platinum wire.

If the solid body 3 is substantially cylindrical, then the tubular sleeve 8 is also cylindrical.

In order to maintain a tight contact between the solid body 3 and the tubular sleeve 8, the internal diameter of the tubular sleeve 8 is substantially equal to the external diameter of the annular sheath 36.

Alternatively, it is possible to provide the solid body 3 in a parallelepipedal shape or any other appropriate shape having means 4 for securing an object to be held and heated, the sleeve 8 being capable of being in heat-conducting contact with the annular sheath 36 through its matching shape.

Advantageously, when the tubular sleeve 8 consists of several tubular segments, it is possible, thanks to the winding of the electric heating member 6 round the tubular sleeve 8, to exert a force of pressure and of compression of the segments of the sleeve 8 on the solid body 3, so as to form a tight contact between the solid body 3 and the sleeve 8.

The assembly means 7 comprise a cylinder 7a tightly surrounding the heating means 5, namely the tubular sleeve 8 and the electric heating member 6 and also comprise removable means 10 for retaining this cylinder 7a.

In a simple manner, the removable retaining means 10 may comprise at least one clamping rod 11 engaged in at least one passageway 12 passing, notably diametrically, through the solid body 3, the annular sheath 36, the heating means 5 and the cylinder 7a.

Preferably, the block 2 of material is in the shape of a pallet capable of being held on the solid body 3 with the aid of securing means 4 comprising two inverted-L sections 13, placed face to face in protrusion on the transverse face 3b of the solid body 3, under which the block 2 of material is inserted.

In order to reinforce the immobilization and securing of the block 2 of material to be tested, the holder 1 of the block 2 of material to be scratched comprises screwing means 37 axially passing through the solid body 3 and capable of exerting a pressing force on the block 2 against the securing means 4. More precisely, a pair of threaded rods 37 is provided that are capable of pressing the block 2 against the sections 13, the rods 37 being respectively capable of being screwed into a pair of tapped holes 38 which axially pass through the solid body 3.

FIG. 2 illustrates a view in section of a device for holding and heating a tip 16 of an indenting apparatus 23 according to the invention, the elements that are identical between the device for holding and heating a block 2 of material to be tested and the device for holding and heating a tip of an indenting apparatus 23 bearing the same reference numbers.

The device 14 for holding and heating a tip 16 of an indenting apparatus 23 has a solid body 3, heating means 5 and assembly means 7, the main difference relating to the securing means 15 between the block 2 of material to be tested and the solid body 3.

The tip 16 is either a Vickers tip, or a Berkovitch tip, or a Knoop tip, or a spherical tip, or a tip of conical or pyramidal shape and is of a type known per se, protruding from the transverse face 3b of the solid body 3.

The securing means 15 between the tip 16 and the solid body 3 may comprise a recess 17 made in the transverse face 3b of the solid body 3 and a core 18 with an outer shape that matches that of the recess 17.

The core 18 comprises a through-passageway 19 with a shape that matches that of the tip 16 so that the latter is received in an adjusted manner in this passageway 19 with its tip 16a protruding from the transverse face 3b of the solid body 3 and its base 16b forced into heat-conducting contact against the bottom 17a of the recess 17.

Means 20 for immobilizing the tip 16 in the through-passageway 19 of the core 18 are also provided and include, according to a preferred embodiment, a powdery material of small particle size placed in the through-passageway 19 between the tip 16 and the core 18, but also between the core 18 and the recess 17. It is for example powdered alumina cement.

Similarly, immobilization means 21 are also provided between the core 18 and the recess 17 of the solid body 3. According to a preferred embodiment, threading means are provided on the outer periphery of the core 18 and tapping means are provided on the inner periphery of the recess 17. Therefore, the recess 17 is tapped and the core 18 is threaded and screwed into the recess 17.

In addition, the bottom 17a of the recess 17 comprises an integral axial finger 22, substantially indistinguishable from the central axis of the solid body 3, protruding and having a diameter at most equal to that of the through-passageway 19, the base 16b of the tip 16 being forced into heat-conducting contact against the transverse face 22a of the finger 22.

Figure 3:
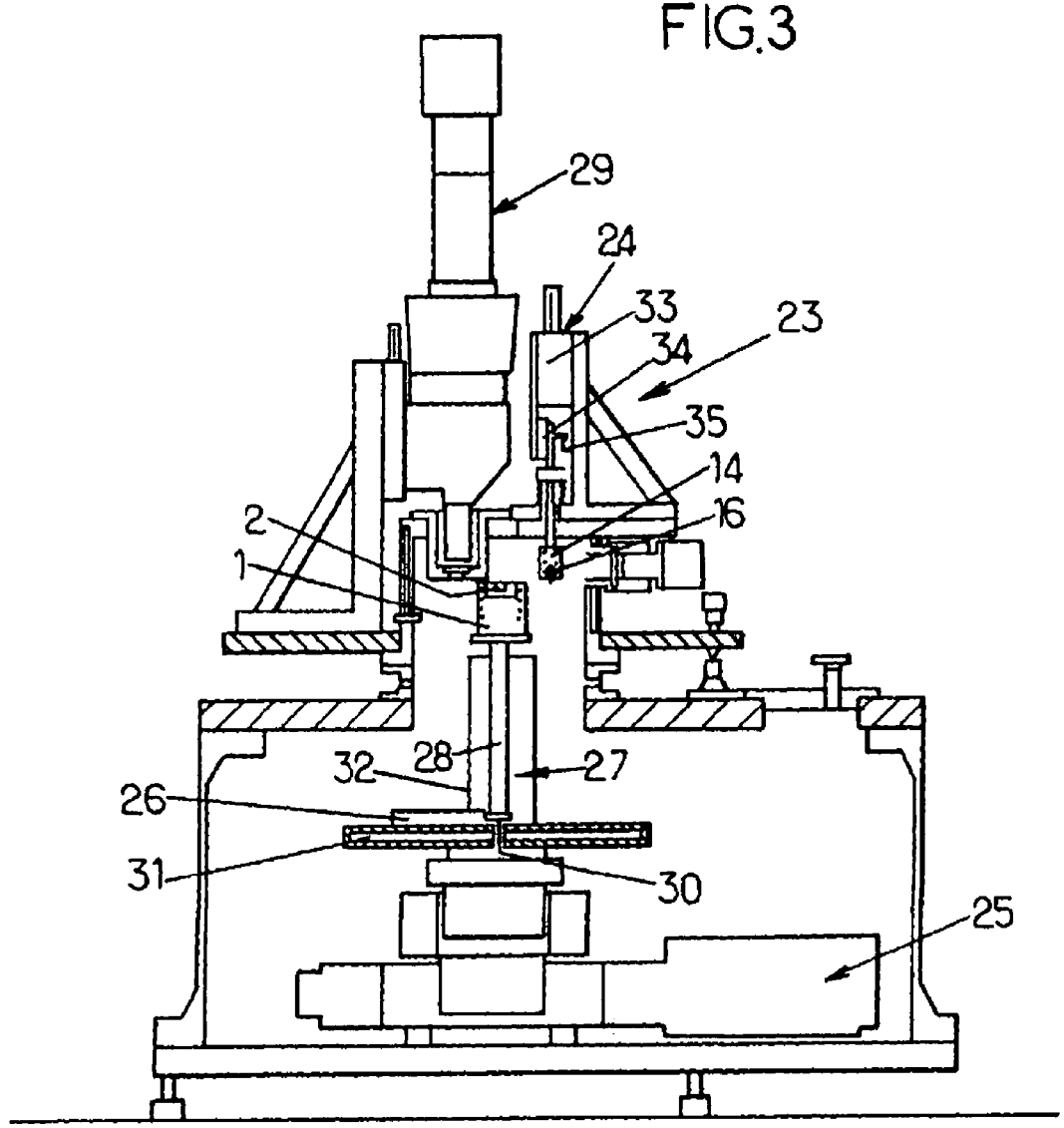
FIG. 3 is a schematic view of an indenting apparatus according to the invention.

FIG. 3 is a schematic view of an indenting apparatus 23 according to the invention, comprising the devices 14,1 for holding and heating a tip 16 and a block 2 of material to be tested as previously described.

The device 14 for holding the tip 16 is advantageously placed facing the device 1 for holding the block of material to be tested so that the tip 16 faces the block 2 of material to be tested that it must punch or scratch.

More precisely, the tip 16 is situated above the block 2 of material to be tested.

In order to allow the tip 16 to make an indentation on the block of material to be tested, the indenting apparatus 23 comprises means 24 for moving the device 14 for holding and heating the tip 16 and means 25 for holding the device 1 for holding and heating a material to be tested.

In order to allow the solid body 3 to be attached either to the means 24 for moving the device 14 for holding and heating the Vickers tip 16, or to the means 25 for holding the device 1 for holding and heating a material to be tested, a rod 3d is provided protruding from the dorsal face 3c of the solid body 3 and advantageously provided on the central axis of the solid body 3.

The protruding rod 3d preferably has a free end that is threaded so as to be able to be screwed onto an element holding either the displacement means 24 or the holding means 25.

Advantageously, a through-pin is provided both in the threaded free end, and also in the element for holding either the displacement means 24 or the holding means 25.

The holder of a block 2 of material to be scratched or punched rests on a force sensor 26, of a type known per se, via connecting means 27 in the form of a tubular element 28, preferably made of zircon.

The deformation of the force sensor 26 is measured continuously by a capacitive displacement sensor 30.

The force sensor 26 rests on a cooled part 31, while the tubular element 28 passes through another cooled part 32.

Preferably, the force sensor 26 consists of a gage bridge device.

The indenting apparatus 23 comprises means 29 for viewing the holder of the block 2 of material to be scratched or punched, notably capable of monitoring the expansion of said holder of the block 2 of material when it is being heated. Specifically, during heating, the device for holding and heating the block 2 of material to be tested expands. Therefore, when the thermal balance is reached and therefore when the temperature is homogeneous within the device for holding the block 2, then the image obtained by the viewing means 29 is stabilized.

The device 14 for holding the tip 16 can be moved vertically with the aid of displacement means 24.

The holder 1 of the block 2 of material to be tested can be moved horizontally with the aid of displacement means 25.

Preferably, the means 24 for vertically moving the holder 14 of the tip 16 comprise a motorized translation table 33 and a piezoelectric translator 34 which is linked to a displacement sensor 35, advantageously a capacitive displacement sensor.

The present invention also relates to a method for measuring the force exerted by a tip 16 on a block 2 of material to be tested with the aid of an indenting apparatus 23.

The method according to the invention comprises a step for measuring the displacement of the tip 16 in the block 2 of material and at the same time a step for measuring the force exerted by the tip 16 on the block 2, said displacement measurement being determined by subtracting the value measured by a first displacement sensor 35 included in the means 24 for displacing the holder 14 of the tip 16 from the value measured by a second displacement sensor 30 measuring the deformation of the force sensor 26 holding the holder 1 of the block 2 of material to be tested.

Preferably, a force feedback loop is formed so long as the value calculated during said measurement step does not reach a fixed setpoint value.

In addition, also provided is a step of displacing the piezoelectric translator 34 included in the means 24 for displacing the holder 14 of the tip 16 so long as the value calculated during said measurement step has not reached the fixed setpoint value.

Preferably, the value of the displacement of the piezoelectric translator 34 corresponds to a percentage of the difference between the fixed setpoint value and the value determined during said measurement step.

Therefore, according to the invention, it is possible to bring the tip to a determined temperature, notably to a temperature substantially equal to that of the block of material to be tested so that, during the test, when the tip is in contact with the material to be tested, there is little or no heat exchange between them. This gives the assurance that the temperature in the location of the test is effectively the predicted temperature.

Furthermore, in order to homogenize the regulation temperature of the device for holding and heating the block 2 of material to be tested and of the tip 16, two cold points (not shown in the figure, but of any type known per se) are placed close to each of the two devices 1, 14. Therefore, the measurement of the temperature is independent for each of the two devices 1, 14 which therefore each have their own regulation and their own heating system. These cold points serve as a reference for the temperature measurement and therefore for the expansion specific to each of the two devices 1, 14. This expansion can be checked when a thermal balance of the two devices 1, 14 is reached.

Means for checking the expansion of the ovens are incorporated into each of the devices 1, 14.

Specifically, since the device for holding and heating the block 2 of material to be tested rests on a force sensor 26, the load detected during heating increases by application of Laplace's law. When the thermal balance is reached, the indication of the force sensor 26 is stabilized.

Furthermore, the immediate proximity of the device for holding the block 2 and the device for holding the tip 16 makes it possible to generate the heating or the cooling of one relative to the other and to form a temperature gradient between the two devices 1, 14, which will create a regulation instability if one of the two devices is at a different temperature from the other.

According to a particular embodiment of the force feedback loop, a file of setpoints is created beforehand. Each setpoint is then read. The feedback loop consists in finding, within a fixed time period, the value of the setpoint. For this, a convergent sequence loop algorithm is used. It involves measuring the difference between the desired value and the measured value. 50% of the difference in force is converted into displacement of the piezoelectric table 34, in order to cause the indenting apparatus to advance into the material, and therefore increase the force. This method is carried out five times in sequence in order to tend toward the desired value. This type of regulation works because an extremely deformable force measurement means is used.

The microscope 29 is used in particular for viewing a precise zone of the block 2 of material to be tested.

By shifting the displacement means 25 by a known quantity, it is possible to test a particular zone of the block of material to be tested and to find this zone in order to measure the imprint left by the tip.

The invention claimed is:

1. An indenting apparatus with a tip suitable for testing a block of material by punching or scratching, comprising:
a tip holder for said tip arranged in the form of a first holding and heating device, notably at a temperature between 700-1200° C., and
a block holder for said block of material to be tested arranged in the form of a second holding and heating device, notably at a temperature between 700-1200° C., said tip holder and said block holder each comprising:
a solid body made of heat-conducting material, having a peripheral side wall and a transverse face;
securing means provided on said transverse face in order to secure in a removable manner either said tip, or said block of material to be tested, in heat-conducting contact with said solid body;
an annular sheath of a shape to match said solid body in which said solid body is housed;
heating means of annular structure suitable for tightly surrounding a peripheral side wall of said annular sheath and being in heat-conducting contact with said annular sheath, said heating means comprising at least one electric heating member, and
assembly means for assembling said solid body and said heating means;

whereby said tip, during a test, is brought to a determined temperature, notably to a temperature substantially equal to that of said block of material to be tested.

2. The indenting apparatus as claimed in claim 1, wherein said heating means comprise a tubular sleeve made of heat-conducting material surrounding said annular sheath and in heat-conducting contact with said peripheral side wall of said annular sheath and said at least one electric heating member is wound round said tubular sleeve.

3. The indenting apparatus as claimed in claim 2, wherein, said at least one electric heating member is a metal wire.

4. The indenting apparatus as claimed in claim 3, wherein said metal wire is helically wound around an outer wall of said tubular sleeve.

5. The indenting apparatus as claimed in claim 2 wherein at least one groove is hollowed out in an outer wall of said tubular sleeve around said tubular sleeve and said at least one heating member is housed in said groove.

6. The indenting apparatus as claimed in claim 1 wherein said assembly means comprise a cylinder tightly surrounding said heating means and removable retaining means for retaining said cylinder.

7. The indenting apparatus as claimed in claim 6, wherein said removable retaining means comprise at least one clamping rod engaged in at least one passageway passing through said solid body, said annular sheath, said heating means and said cylinder.

8. The indenting apparatus as claimed in claim 1 wherein said securing means for securing said tip comprise:
a recess made in said transverse face of said solid body;
a core with an outer shape that matches that of said recess said core comprising a through-passageway with a shape to match that of said tip so that said tip is received in an adjusted manner in said-though passageway with a pointed end of said tip protruding outside said transverse face of said solid body and a base of said tip forced into heat-conducting contact against a bottom of said recess;
first immobilizing means for immobilizing said tip in said through-passageway; and
second immobilizing means for immobilizing said core in said recess.

9. The indenting apparatus as claimed in claim 8, wherein said bottom of said recess comprises a protruding integral axial finger with a diameter at most equal to a diameter of said through-passageway, and said base of said tip is forced into heat-conducting contact against a transverse face of said finger.

10. The indenting apparatus as claimed in claim 8 wherein said recess is tapped and in that said core is threaded and screwed into said recess.

11. The indenting apparatus as claimed in claim 8 wherein said first immobilizing means comprise a powdery material of small particle size placed in said through-passageway between said tip and said core.

12. The indenting apparatus as claimed in claim 1 wherein said securing means for securing said block of material to be tested comprise two inverted-L sections placed face to face in protrusion on said transverse face of said solid body, under which said block of material is inserted.

13. The indenting apparatus as claimed in claim 1 wherein said tip is selected from the group comprising a Vickers tip, a Berkovitch tip, a Knoop tip, and a spherical tip.

14. The indenting apparatus as claimed in claim 1 wherein said block holder rests on a force sensor.

15. The indenting apparatus as claimed in claim 14, wherein said block holder rests on said force sensor via connecting means in the form of a tubular.

16. The indenting apparatus as claimed in claim 14 wherein the deformation of said force sensor is measured continuously by a capacitive displacement sensor.

17. The indenting apparatus as claimed in claim 14 characterized in that wherein said force sensor rests on a cooled part.

18. The indenting apparatus as claimed in claim 15 wherein said tubular element passes through a cooled part.

19. The indenting apparatus as claimed in claim 14 wherein said force sensor consists of a gage bridge device.

20. The indenting apparatus as claimed in claim 1 comprising viewing means for viewing said block holder and capable of monitoring the expansion of said block holder of the block of material when it said block holder is being heated.

21. The indenting apparatus as claimed in claim 1 wherein said block holder comprises screwing means passing axially through said solid body and capable of applying a pressing force on said block against said securing means.

22. The indenting apparatus as claimed in claim 1 wherein said tip holder can be moved vertically with the aid of vertical displacement means.

23. The indenting apparatus as claimed in claim 1, wherein said block holder can be moved horizontally with the aid of horizontal displacement means.

24. The indenting apparatus as claimed in claim 22 wherein said vertical displacement means of said tip holder comprise a motorized translation table and a piezoelectric translator.

25. The indenting apparatus as claimed in claim 22 wherein said piezoelectric translator is linked to a displacement sensor.

26. A method of measuring the force exerted by a tip on a block of material to be tested with the aid of an indenting apparatus, the method comprising a step of heating said tip with the aid of heating means so that said tip is brought, during a test, to a determined temperature, notably to a temperature substantially equal to that of said block of material to be tested, a step of measuring the displacement of said tip in said block of material and, at the same time, a step of measuring the force exerted by said tip on said block said displacement measurement being determined by subtracting the value measured by a first displacement sensor included in the means for displacing a holder of said tip from the value measured by a second displacement sensor measuring the deformation of a force sensor holding a holder of said block of material to be tested.

27. The method for measuring the force as claimed in claim 26, wherein a force feedback loop is formed so long as the value calculated during said measurement step does not reach a fixed setpoint value.

28. The method for measuring the force as claimed in claim 27, further comprising a step of displacing a piezoelectric translator included in the said means for displacing said holder of said tip so long as the value calculated during said measurement step has not reached said fixed setpoint value.

29. The method of measuring the force as claimed in claim 28, wherein the value of the displacement of said piezoelectric translator corresponds to a percentage of the difference between the fixed setpoint value and the value determined during said measurement step.

* * * * *